United States Patent
Kloster

(10) Patent No.: US 10,299,884 B2
(45) Date of Patent: May 28, 2019

(54) SPRING DRIVEN PUMP FOR DISPENSING DISCRETE BURSTS OF LIQUID

(71) Applicant: KONINKLIJKE PHILIPS N.V., Eindhoven (NL)

(72) Inventor: Tyler G. Kloster, Snoqualmie, WA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 880 days.

(21) Appl. No.: 14/407,771

(22) PCT Filed: Jun. 11, 2013

(86) PCT No.: PCT/IB2013/054774
§ 371 (c)(1),
(2) Date: Dec. 12, 2014

(87) PCT Pub. No.: WO2013/190428
PCT Pub. Date: Dec. 27, 2013

(65) Prior Publication Data
US 2015/0164612 A1      Jun. 18, 2015

Related U.S. Application Data

(60) Provisional application No. 61/740,548, filed on Dec. 21, 2012, provisional application No. 61/663,008, filed on Jun. 22, 2012.

(51) Int. Cl.
*A61C 1/00* (2006.01)
*A61H 9/00* (2006.01)
(Continued)

(52) U.S. Cl.
CPC ........ *A61C 1/0092* (2013.01); *A61C 17/0202* (2013.01); *A61C 17/028* (2013.01); *A61H 9/0007* (2013.01); *A61H 13/00* (2013.01)

(58) Field of Classification Search
CPC .... A61C 17/02; A61C 17/0202; A61C 17/028
See application file for complete search history.

(56) References Cited

U.S. PATENT DOCUMENTS 3,425,410 A    2/1969   Cammack
3,966,359 A *  6/1976   Woog ................... A46B 13/06
                                                    417/38
(Continued)

FOREIGN PATENT DOCUMENTS

EP         1201201 A2    5/2002
JP      2012513795 A    6/2012
(Continued)

*Primary Examiner* — LaToya M Louis

(57) ABSTRACT

An oral care appliance (10) having a pump assembly (14) for delivering discrete bursts or shots of liquid. The pump assembly includes a pump housing (36) and an inlet/outlet assembly (38) at a forward end of the housing, including one-way valves (80, 82) in the inlet and outlet openings. A plunger sleeve (44) is positioned within the housing with a central opening (48) in a fluid-tight relationship with the inlet and outlet assembly. A plunger (52) includes a center portion (56), positioned in the central opening of the plunger sleeve in a fluid-tight relationship therewith. The plunger sleeve includes an outer member (54) between the plunger sleeve and the internal surface of the housing. A compressible spring (64) is positioned between a forward end of the outer member of the plunger and the rear end of the housing. A drive mechanism (72) moves the plunger rearwardly, resulting in the plunger sleeve filling with liquid by vacuum action from a reservoir (26) in the appliance, and then releases the plunger, allowing the spring to move the plunger quickly forward, forcing liquid in the plunger sleeve out through the fluid outlet in a direct burst.

18 Claims, 2 Drawing Sheets

(51) Int. Cl.
    *A61H 13/00*     (2006.01)
    *A61C 17/02*     (2006.01)
    *A61C 17/028*     (2006.01)

(56) References Cited

U.S. PATENT DOCUMENTS

| | | | | |
|---|---|---|---|---|
| 5,224,500 | A * | 7/1993 | Stella | A61C 15/047 132/322 |
| 6,637,584 | B2 * | 10/2003 | Takahashi | B65G 25/06 198/540 |
| 8,753,117 | B2 * | 6/2014 | Edwards | A61C 1/0084 239/359 |
| 2002/0058231 | A1 * | 5/2002 | Friedman | A61O 5/62 433/90 |
| 2002/0082545 | A1 | 6/2002 | Sennett et al. | |
| 2009/0095777 | A1 | 4/2009 | Francavilla | |
| 2009/0299328 | A1 | 12/2009 | Mudd et al. | |
| 2011/0244418 | A1 * | 10/2011 | Edwards | A61C 1/0084 433/90 |
| 2012/0141952 | A1 * | 6/2012 | Snyder | A61C 17/02 433/82 |
| 2013/0122453 | A1 * | 5/2013 | Paxton | A61B 1/24 433/29 |

FOREIGN PATENT DOCUMENTS

| | | |
|---|---|---|
| WO | 02064055 A1 | 8/2002 |
| WO | 2006076921 A1 | 7/2006 |
| WO | 2007064885 A2 | 6/2007 |
| WO | 2010076694 A1 | 7/2010 |
| WO | 2012042445A1 A1 | 4/2012 |

* cited by examiner

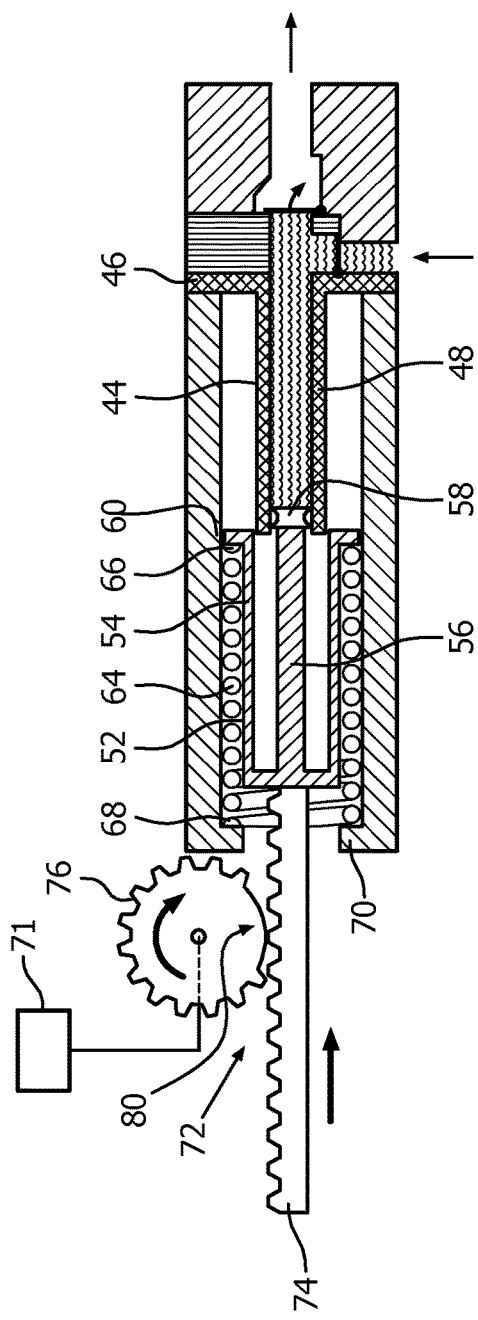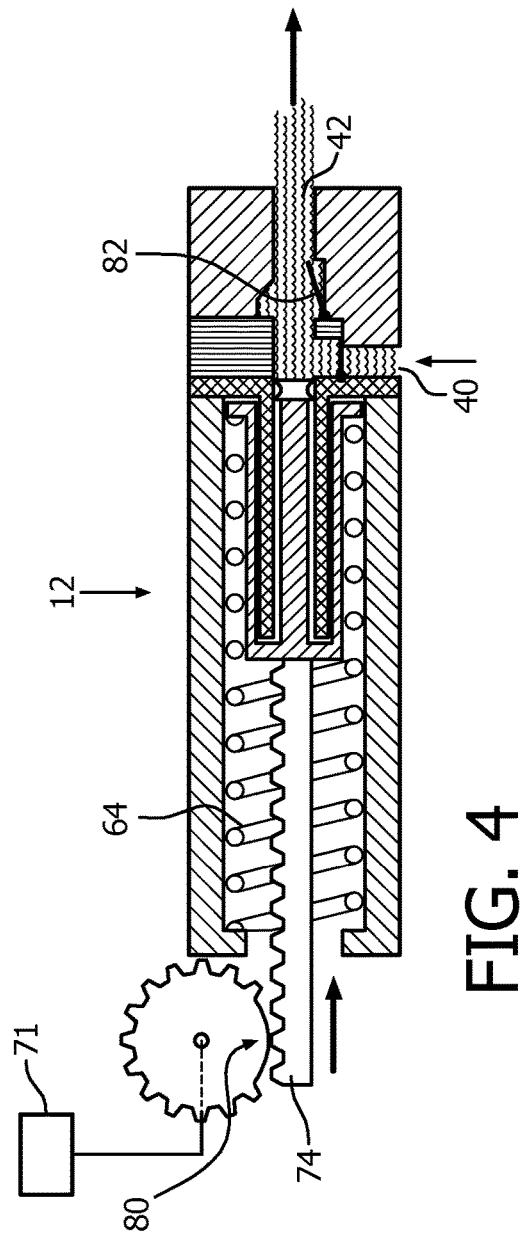
FIG. 3
FIG. 4

SPRING DRIVEN PUMP FOR DISPENSING DISCRETE BURSTS OF LIQUID

CROSS-REFERENCE TO PRIOR APPLICATIONS

This application is the U.S. National Phase application under 35 U.S.C. § 371 of International Application No. PCT/IB2013/054774, filed on Jun. 11, 2013, which claims the benefit of U.S. Provisional Patent Application No. 61/740,548, filed on Dec. 21, 2012, which claims benefit of U.S. Provisional Patent Application No. 61/663,008, filed on Jun. 22, 2012. These applications are hereby incorporated by reference herein.

TECHNICAL FIELD

This invention relates generally to spring driven pumps and more specifically concerns a pump for dispensing discrete bursts or shots of liquid, such as for cleaning teeth.

BACKGROUND OF THE INVENTION

There are many systems/devices known for cleaning teeth, including various ones using brushes, as well as others which use liquid droplets or liquid pulses. One other approach to cleaning teeth uses discrete bursts or shots of liquid to generate hydrodynamic cavitation, or a non-cavitating jet of liquid. However, there are no known/commercially available pumps which can efficiently accomplish short bursts of liquid in an efficient manner for a hand-held appliance. Pumps are available that can provide the required pressures, e.g. 8-10 bar, but these produce a constant or relatively constant, flow, as opposed to producing discrete separate bursts of liquid in response to operation of an actuation switch on the appliance. While it is possible to use a pump to re-circulate a flow of liquid to create a sequence of discrete bursts, such an arrangement requires an excessive amount of power that is not available in a hand-held consumer appliance.

Accordingly, it is desirable to have a pump which is capable of producing discrete bursts or shots of liquid in a hand-held appliance useful in cleaning teeth.

SUMMARY OF THE INVENTION

Accordingly, an oral care appliance, comprises: an appliance housing; an elongated neck and nozzle assembly; a reservoir for liquid; and a pump assembly for delivering discrete bursts of liquid to the neck and nozzle assembly, the pump assembly including a pump housing, a liquid inlet/outlet assembly at a forward end of the pump assembly, a cylindrical shaped plunger sleeve having a central opening, a plunger assembly having a center plunger element which includes a fluid-tight seal at a forward end thereof, positionable within the central opening of the plunger sleeve, a compressible spring positioned between a forward end of the plunger assembly and a rear end of the housing, and a drive mechanism controlled by an actuator for moving the plunger assembly rearwardly and then releasing it, wherein the inlet/outlet assembly includes a one-way liquid inlet valve and a one-way liquid outlet valve in fluid communication with the central opening of the plunger sleeve, such that in operation the drive mechanism moves the plunger assembly to the rear, drawing liquid into the plunger sleeve, and then releasing the plunger assembly, forcing liquid out through the inlet/outlet assembly to the neck and nozzle assemblies, for a single burst of liquid.

BRIEF DESCRIPTION OF THE DRAWINGS

FIG. 3 is a cross-section view of the pump of FIG. 1 at a second stage of operation.

FIG. 4 is a cross-section of the pump at a third and last stage of operation where bursts of liquid proceed from an outlet.

BEST MODE FOR CARRYING OUT THE INVENTION

Figure 1:
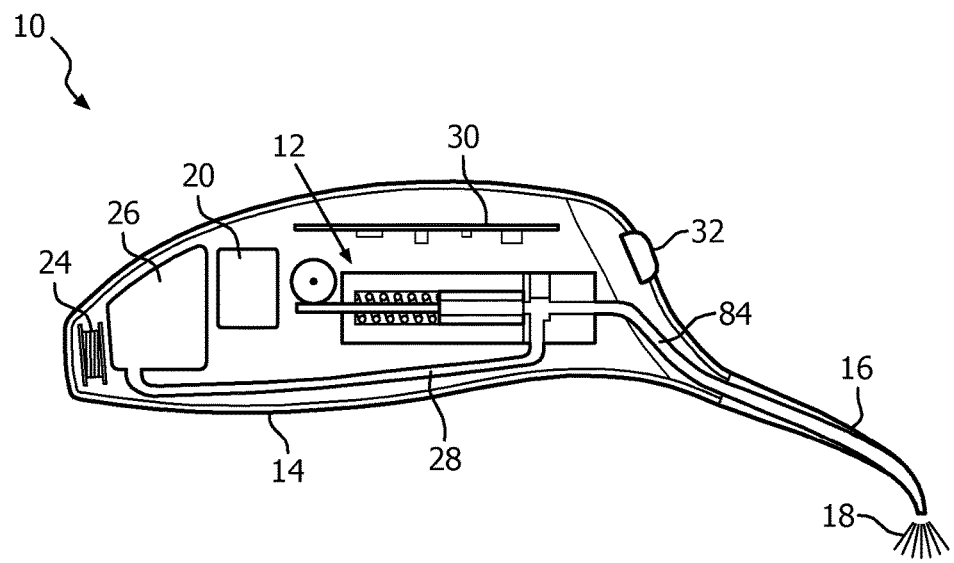
FIG. 1 is a cross-section view of an entire appliance showing the pump for the appliance.

FIG. 1 shows an oral care appliance 10 with a discrete liquid burst pump 12. The appliance generally includes an appliance body 14, an elongated neck 16 and an outlet nozzle 18. The appliance also includes a rechargeable battery 20 and a charging coil 24, which drives pump 12. A water reservoir 26 supplies liquid to the pump via an inlet line 28. A printed circuit board 30 contains a microprocessor/controller for operating the appliance. An activation switch 32 controls the periodic actuation of the pump, which in operation produces a series of discrete bursts or shots of liquid from nozzle 18. Typically, the liquid bursts occur on a once/twice per second intervals, although this can be varied to some extent.

Figure 2:
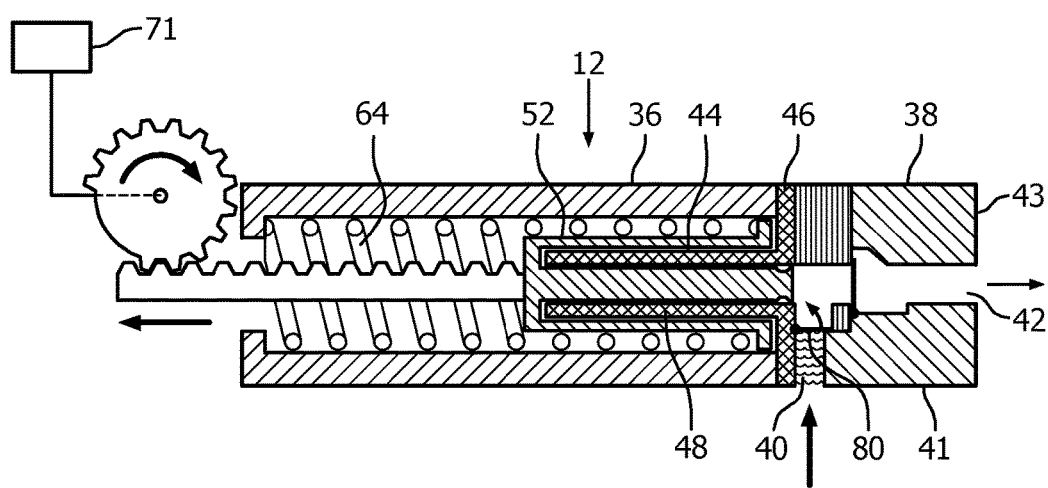
FIG. 2 is a cross-section view showing the pump of FIG. 1 at a first stage of operation.

Referring now to FIGS. 2-4, the pump 12 includes a housing 36, which can vary in length and width, but is convenient to hold in the hand. The housing is hollow in the embodiment shown. The pump includes an inlet/outlet assembly 38 at the forward end of the housing 36. A liquid inlet, in the side 41 of the inlet/outlet assembly has a diameter which can vary between 0.5 mm and 5 mm. Attached to the inlet opening 40 is inlet line 28, as shown in FIG. 1. The inlet/outlet assembly also includes an outlet opening 42, which is approximately central of the forward end 43 of the inlet/outlet assembly. The outlet opening also can vary between 0.5 and 5 mm. Both the housing 36 and the inlet and outlet assembly are typically made of plastic, but could also be made of other materials. Positioned in pump housing 36 is a plunger sleeve 44. Plunger sleeve 44 includes a base portion 46 and a hollow central portion 48 which extends into the housing approximately one-half the length of the housing. The base portion is sealed to the forward end of the housing and rear end of inlet/outlet assembly, providing a fluid-tight connection therebetween. The interior of the central portion is in fluid communication with the inlet opening 40 and the outlet opening 42.

The pump also includes a cylindrical plunger 52 with an outer cylindrical portion 54 and a center leg portion 56. At a forward end of center portion 56 is a fluid sealing element 58 (FIG. 3). At a forward end of the outer portion 54 of plunger 52 is a ring-like ear element 60 which extends from the outer member 54 to the internal surface of housing 36 and fluid seals plunger 52 against the housing.

Plunger 52 is configured so that the center leg portion 56 with seal 58 fits inside the central portion of plunger sleeve 46, while the outer cylindrical portion 54 fits between the outer surface of the center portion 48 of plunger sleeve 46 and the pump housing, so that in operation, plunger 52 moves back and forth within the housing, with center portion 56 and seal 58 moving back and forth within the plunger sleeve 46. The housing, the plunger sleeve and the plunger are all coaxial, which is an important consideration in terms of the overall configuration and operation of the pump.

Positioned between the outer portion 54 of the plunger and the internal surface of the housing is a compressible spring 64. The forward end 66 of spring 64 is positioned against ear element 60, while the rear end 68 of spring 60 is positioned against an inwardly extending portion 70 of the pump housing.

The pump also includes a motor assembly for moving plunger 52 to the rear of the pump. In the embodiment shown, this includes a motor shown generally at 71 and a rack and pinion assembly 72. Rack portion 74 is attached to the rear end of the plunger, while the pinion (gear) portion 76 has a set of teeth 78 arranged around its periphery, with a section of teeth 80 missing, so that in operation, as the pinion moves the rack to the rear a selected distance, compressing the spring, the missing teeth section will be encountered at a point, resulting in a release of the plunger, which moves quickly forward under the force of the compressed spring.

In FIG. 2, the plunger is at its most forward position, adjacent the forward end of the housing and against the base portion of the plunger sleeve. As the rack moves to the rear (shown in FIG. 3), by action of the motor and gear, a partial vacuum is created in the inlet/outlet assembly, resulting in liquid being drawn from the liquid reservoir 26 through inlet line 28 and a one-way valve 80 positioned in the inlet opening 40. FIG. 3 shows rack 74 retracted all the way to the rear, just prior to release. In this position, liquid has filled the center portion 48 of plunger sleeve 44. The amount of the liquid can vary, between 0.5 ml and 5 ml, depending upon the internal dimensions of the plunger sleeve. The overall length of the stroke of the plunger can vary, between 30 and 60 mm. FIG. 3 shows the rack (and the plunger) moved to the rear, just prior to the portion of missing teeth on the pinion gear being encountered. Although the embodiment shown is a rack and pinion drive, other drive arrangements could be used, including a screw drive, for example.

FIG. 4 shows the plunger after it has been released and moved back to its original position as the plunger moves under the force of the spring. Liquid is driven out of the plunger sleeve and through liquid outlet 42, which also includes a one-way valve 82. Referring again to FIG. 1, liquid proceeds through a connecting line in the elongated neck 16 and out nozzle 18.

The pump is now ready for the next shot or burst of liquid, controlled by the actuation assembly 32. The liquid pressure is typically less than or approximately 50 psi, but can vary between 10 psi and 100 psi or more. The result is that bursts of liquid, typically 0.2-0.5 ml but in some cases up to 5 ml, occur at intervals of one to two times per second. The power necessary to drive the liquid pump is less than that of a conventional pump, as the energy needed to compress the spring is imparted over a relatively long period of time, i.e. a second or so, versus the energy release, which is on the order of 10-20 milliseconds.

Accordingly, an oral care appliance using a special pump to produce discrete, physically separate bursts or shots of liquid is disclosed. Because of the particular arrangement and structure of the pump, the appliance can be hand-held, without a direct connection to the source of external power.

Although a preferred embodiment has been disclosed for purposes of illustration, it should be understood that various changes, modifications and substitutions may be incorporated in the preferred embodiment without departing from the spirit of the invention as defined by the claims which follow:

What is claimed is:

1. An oral care appliance, comprising:
an appliance housing;
an elongated neck and nozzle assembly;
a reservoir for liquid; and
a pump assembly configured to deliver discrete bursts of liquid to the elongated neck and nozzle assembly, the pump assembly including a pump housing, a liquid inlet/outlet assembly at a forward end of the pump assembly, a cylindrical shaped plunger sleeve having a central opening, a plunger assembly having a center portion which includes a fluid-tight seal at a forward end thereof, positionable within the central opening of the plunger sleeve, a compressible spring positioned between a forward end of the plunger assembly and a rear end of the housing, and a drive mechanism controlled by an actuator for moving the plunger assembly rearwardly and then releasing it, wherein the drive mechanism includes a rack and pinion assembly with a section of missing teeth on a pinion gear of the rack and pinion assembly, wherein the rack of the rack and pinion assembly is located at least partially within the compressible spring, wherein the inlet/outlet assembly includes a one-way liquid inlet valve and a one-way liquid outlet valve in fluid communication with the central opening of the plunger sleeve, wherein the oral care appliance is configured such that in operation the drive mechanism moves the plunger assembly to the rear, drawing liquid into the plunger sleeve, and then releasing the plunger assembly, forcing liquid out through the inlet/outlet assembly to the neck and nozzle assemblies defining a single burst of liquid.

2. The appliance of claim 1, including fluid seals at the liquid inlet and the liquid outlet, and wherein the fluid inlet and outlet assemblies are in a fluid-tight relationship relative to the center portion of the plunger sleeve.

3. The appliance of claim 1, wherein the pressure of the liquid outflow is in the range of 10-200 psi.

4. The appliance of claim 3, wherein the pressure is in the range of 6-10 bar.

5. The appliance of claim 1, wherein the appliance is arranged so as to deliver from one to two bursts per second.

6. The appliance of claim 1, wherein the spring is compressed over at least one second, but fully releases in 10-20 milliseconds.

7. The appliance of claim 1, wherein the liquid inlet opening and liquid outlet opening are within the range of ½ mm to 5 mm.

8. The appliance of claim 1, wherein the volume of liquid in each burst is within the range of 0.2 ml to 5 ml.

9. The appliance of claim 1, wherein the plunger moves linearly within the range of 30-60 mm.

10. An oral care appliance, comprising:
an appliance housing;
an elongated neck and nozzle assembly;
a reservoir for liquid; and
a pump assembly configured to deliver discrete bursts of liquid to the elongated neck and nozzle assembly, the pump assembly including a pump housing, a liquid inlet/outlet assembly at a forward end of the pump assembly, a cylindrical shaped plunger sleeve having a central opening, a plunger assembly having a center portion which includes a fluid-tight seal at a forward end thereof, positionable within the central opening of the plunger sleeve, a compressible spring positioned between a forward end of the plunger assembly and a rear end of the housing, and a drive mechanism controlled by a motor driven actuator for moving the plunger assembly rearwardly and then releasing it, wherein the drive mechanism includes a rack and pinion assembly with a pinion gear of the rack and pinion assembly having a section of missing teeth, wherein the rack of the rack and pinion assembly is located at least partially within the compressible spring, wherein the inlet/outlet assembly includes a one-way liquid inlet valve and a one-way liquid outlet valve in fluid communication with the central opening of the plunger sleeve, wherein the oral care appliance is configured such that in operation the drive mechanism moves the plunger assembly to the rear, until the drive mechanism reaches a preselected position, drawing liquid into the plunger sleeve, and then releasing the plunger assembly, forcing liquid out through the inlet/outlet assembly to the neck and nozzle assemblies, defining a single burst of liquid.

11. The appliance of claim 10, including fluid seals at the liquid inlet and the liquid outlet, and wherein the fluid inlet and outlet assemblies are in a fluid-tight relationship relative to the center portion of the plunger sleeve.

12. The appliance of claim 10, wherein the pressure of the liquid outflow is in the range of 10-200 psi.

13. The appliance of claim 12, wherein the pressure is in the range of 6-10 bar.

14. The appliance of claim 10, wherein the appliance is arranged so as to deliver from one to two bursts per second.

15. The appliance of claim 10, wherein the spring is compressed over at least one second, but fully releases in 10-20 milliseconds.

16. The appliance of claim 10, wherein the liquid inlet opening and liquid outlet opening are within the range of ½ mm to 5 mm.

17. The appliance of claim 10, wherein the volume of liquid in each burst is within the range of 0.2 ml to 5 ml.

18. The appliance of claim 10, wherein the plunger moves linearly within the range of 30-60 mm.

* * * * *